(12) United States Patent
Moersdorf et al.

(10) Patent No.: US 8,821,414 B2
(45) Date of Patent: Sep. 2, 2014

(54) DEVICE AND METHOD FOR PREDICTING A LOSS OF CONTROL OVER A MUSCLE

(75) Inventors: Hans-Joachim Moersdorf, Fuerth (DE);
Stefan Aschenbrenner, Eckental (DE);
Joern Thielecke, Erlangen (DE);
Hubert Schmitt, Erlangen (DE)

(73) Assignees: Fraunhofer-Gesellschaft zur Foerderung der Angewandten Forschung E.V., Munich (DE);
Friedrich-Alexander-Universitaet Erlangen-Nuernberg, Erlangen (DE)

( * ) Notice: Subject to any disclaimer, the term of this patent is extended or adjusted under 35 U.S.C. 154(b) by 1020 days.

(21) Appl. No.: 12/668,016

(22) PCT Filed: Jun. 16, 2008

(86) PCT No.: PCT/EP2008/004832
§ 371 (c)(1),
(2), (4) Date: Jul. 22, 2010

(87) PCT Pub. No.: WO2009/006980
PCT Pub. Date: Jan. 15, 2009

(65) Prior Publication Data
US 2010/0286572 A1    Nov. 11, 2010

(30) Foreign Application Priority Data

Jul. 11, 2007 (DE) .......................... 10 2007 032 268
Aug. 14, 2007 (DE) .......................... 10 2007 038 392

(51) Int. Cl.
*A61B 7/00* (2006.01)
*A61B 5/103* (2006.01)
*A61B 5/117* (2006.01)

(52) U.S. Cl.
USPC ............................................ 600/586; 600/595

(58) Field of Classification Search
USPC ......... 600/595, 594, 587, 534, 528, 527, 431, 600/586
See application file for complete search history.

(56) References Cited

U.S. PATENT DOCUMENTS

| 4,748,987 A | 6/1988 | Barry |
| 4,805,636 A | 2/1989 | Barry et al. |

(Continued)

FOREIGN PATENT DOCUMENTS

| DE | 196 37 383 A1 | 4/1998 |
| DE | 10 2006 002 114 A1 | 6/2007 |

(Continued)

OTHER PUBLICATIONS

Meyers Großes Konversations-Lesikon, Leipzig 1905-1909, Band 14; retrieved online May 9, 2008 at zeno.org; http://www.zeno.org/Meyers-1905/A/Muskeln; pp. 319-323.

(Continued)

*Primary Examiner* — Max Hindenburg
*Assistant Examiner* — Jonathan M Foreman
(74) *Attorney, Agent, or Firm* — Perkins Coie LLP; Michael A. Glenn

(57) ABSTRACT

A device for predicting a loss of control over a muscle of a human being has a detector for detecting a sound of the muscle, an acquirer for acquiring an acceleration of the human being and an evaluator for evaluating the sound and the acceleration to determine an imminent loss of control over the muscle from the sound and the acceleration.

26 Claims, 9 Drawing Sheets

(56) References Cited

U.S. PATENT DOCUMENTS

| | | | | |
|---|---|---|---|---|
| 5,917,414 | A | * | 6/1999 | Oppelt et al. ............... 600/301 |
| 6,477,406 | B1 | | 11/2002 | Turcott |
| 7,177,686 | B1 | | 2/2007 | Turcott |
| 7,537,573 | B2 | * | 5/2009 | Horst ........................ 600/595 |
| 2004/0049132 | A1 | * | 3/2004 | Barron et al. ............... 600/595 |
| 2004/0127807 | A1 | | 7/2004 | Hatlesad et al. |
| 2005/0043652 | A1 | * | 2/2005 | Lovett et al. ............... 600/595 |
| 2006/0052720 | A1 | * | 3/2006 | Ross et al. .................. 600/595 |
| 2007/0208232 | A1 | * | 9/2007 | Kovacs ...................... 600/595 |
| 2008/0009772 | A1 | * | 1/2008 | Tyler et al. ................. 600/595 |

FOREIGN PATENT DOCUMENTS

| | | | |
|---|---|---|---|
| EP | 1 408 443 | A1 | 4/2004 |
| JP | 2004364009 | | 12/2004 |
| JP | 2004364009 | A * | 12/2004 |
| JP | 2007167185 | | 5/2007 |
| JP | 2007142540 | | 7/2007 |

OTHER PUBLICATIONS

Axisa F. et al: "Flexible Technologies and Smart Clothing for Citizen Medicine, Home Healthcare, and Disease Prevention", Sep. 1, 2005, IEEE Transactions on Information Technology in Biomedicine, IEEE Service Center, Los Alamitos, CA U.S. vol. 9, No. 3, pp. 325-336 XP011138579, ISSN: 1089-7771.

Pascal Madeleine et al: "Spectral moments of mechanomyographic signals recorded with accelerometer and microphone during sustained gatiguing contractions", Medical & Biological Engineering & Computing, Springer, Berlin, DE, vol. 44, No. 4, Apr. 1, 2006, p. 290-297, XP019360730, ISSN: 1741-0444.

Silva J. et al: "Coupled microphone-accelerometer sensor pair for dynamic noise reduction in MMG signal recording", Electronics Letters, IEEE Electronics Letters; Stevenage, GB, vol. 39, No. 21, Oct. 16, 2003, p. 1496-1498, XP006021196, ISSN: 0013-5194.

* cited by examiner

DEVICE AND METHOD FOR PREDICTING A LOSS OF CONTROL OVER A MUSCLE

CROSS-REFERENCE TO RELATED APPLICATIONS

This application is a national phase entry of PCT Patent Application No. PCT/EP2008/004832, filed 16 Jun. 2008, which claims priority to German Patent Application No. 10 2007 032 268.4, filed 11 Jul. 2007 and German Patent Application No. 10 2007 038 392.6 filed 14 Aug. 2007, each of which is incorporated herein by reference.

BACKGROUND OF THE INVENTION

The present invention relates to a device and to a method for predicting a loss of control over a muscular system and, in particular, to detecting vertiginous attacks and tiredness. Vertiginous attacks may, for example, occur in the approach to a fall during which states of muscle fatigue may occur, for example as a consequence of physical strain or tiredness—like, for example, while driving a car. Further fields of application include recognizing a loss of control under the influence of drugs or alcohol, for example, and, maybe, recognizing degenerative neurological diseases, like, for example, Parkinson's disease.

Many elderly people wish to be able to live in their apartments for as long as possible. However, for the relatives and medical personnel, the question arises as to how an abruptly altered physical condition, for example, can be recognized. A frequent problem is that, for example, when senior citizens fall, they might be lying on the ground helplessly. Numerous efforts have been made to recognize such a situation by means of a fall detector, for example, so that help can be requested automatically. These efforts include, for example, detection of a fall by means of acceleration and/or position sensors. Thus, an alarm is triggered when a certain threshold value is exceeded, like, for example, when hitting the ground. Further conventional methods try to additionally evaluate the spatial position of the human being or possible movement patterns following a preceding fall event using position sensors in order to achieve higher reliability and rule out false alarms. However, it has shown that a fall or staggering can only be determined after the event by means of conventional devices or methods, and thus the fall itself can hardly be avoided. A device able to "foresee" a fall or staggering would be better in order to be able to prevent that very fall. Predicting meant of this kind may, apart from the syndromes aimed at, also be applied in order to prevent a loss of control as the result of over-tiredness, for example.

SUMMARY

According to an embodiment, a device for predicting a loss of control over a muscle of a human being may have: means for detecting a muscle sound; means for acquiring an acceleration of the human being; and means for evaluating the sound and the acceleration to determine an imminent loss of control over the muscle from the sound and the acceleration.

According to another embodiment, a method for predicting a loss of control over a muscle of a human being may have the steps of: detecting a muscle sound; acquiring an acceleration of the human being; and evaluating the sound and the acceleration in order to determine an imminent loss of control over the muscular system from the sound and the acceleration.

Another embodiment may have a computer program comprising a program code for performing the method for predicting a loss of control over a muscle of a human being as mentioned above when the program runs on a computer.

The present invention is based on the finding that an imminent loss of control over a muscle of a human being or of a human body announces itself through a change of sounds or sound pattern in the muscular system which in turn may be accompanied by staggering movements. Thus, a loss of control over a muscle (like, for example, a supportive muscle or leg muscles) can be predicted by means detecting sounds of the muscle and different means acquiring an acceleration of, for example, the human body or the head. The data detected (muscle sounds and acceleration) can be evaluated in an evaluating unit such that an imminent loss of control over the muscles can be predicted from the (typical) sounds of the muscles and the acceleration.

Thus, embodiments of the present invention include fusing muscle sound data and acceleration measurement data so that it will be possible in principle to warn a human being under observation already before falling.

Taking a measurement value may, for example, take place in two ways:
(a) individual sensors for acquiring muscle sounds and body acceleration are attached to the human body separately;
(b) a combined sensor including the sound sensor and the acceleration sensor is attached to a position of the human body.

In case (b) in which the sensors are implemented as a combined sensor, attachment to the thigh of the human being seems to be practical. Both detecting movement patterns and detecting a loss in tone which may cause potential staggering are possible here. A quality of regulating the muscle tone (muscle tension) is determined by maintaining an operating point which is determined by an equilibrium between the gravitational component and the force effect as a result of the muscle tension. With a high-quality tone, the muscle tension is high enough so as to withstand gravity, on the other hand, however, low enough so as to enable harmonic movement. A cramp, for example, is a strong over-increase in tone and paralysis, for example, represents a loss of tone.

Movement patterns may, for example, indicate standing, walking or running or also climbing stairs and may consequently be detected as such in the evaluating unit. Apart from fixing the combined sensor to the thigh of the human body, optionally other positions of the human body may be used for placing the combined sensor—for example the torso or the neck/shoulder area. At present, however, fixing to the thigh of the human being seems to be practical.

In case (a) in which the sensors (acceleration sensor, sound sensor) are implemented as individual sensors, it seems to be obvious to place a microphone (as a sound sensor) for recording the muscle sounds, in this case too, to the thigh and to attach the acceleration sensor to the hip of the human being. Thus, movements of the torso (for example as a result of a fall, rotation, etc.) can be classified. In further embodiments, the individual sensors may, here too, be placed at different positions which are, for example, selected so as to correspond to a specific case of application.

Apart from the possibility, as already mentioned, of being used as predicting means able to warn of an imminent fall, embodiments may, for example, determine vertiginous attacks caused by the heart. This may, for example, take place by means of another sensor for detecting cardiomuscular sounds which registers the vertiginous attacks caused by the heart, which occur frequently in elderly people, even before the onset of a manifest vertiginous attack and which is able to intervene by means of a preventive method. The preventive method may, for example, include a corresponding alarm signal so that measures may be taken or a warning be issued when a vertiginous attack is approaching.

Apart from these symptoms caused by age and/or disease, embodiments of the present invention are also suitable for recognizing tiredness, for example when driving a car, and detecting same using nodding movements of the head. For this scenario of application, the sound sensor and/or acceleration sensor may, for example, be placed on the head or in the neck/shoulder area. Apart from signs of tiredness when driving a vehicle, muscular states of tiredness—for example after physical strain (like, for example, climbing stairs)—can also be detected when approaching, and a corresponding alarm can go off. Depending on which body region is affected by the physical strain, sensors may be positioned correspondingly.

Thus, embodiments try to foresee a critical situation and recognize vertigo, states of fatigue, tiredness, etc. already occurring and the accompanying short staggering movement caused by a loss in tone in the posture muscles.

Apart from the sensors, embodiments also comprise an evaluating unit which may exemplarily be integrated into a casing of the combined sensor or into a casing of one of the individual sensors (of the movement sensor or the sound sensor). The evaluating unit acquires the data of the sensors detected and may further make use of "intelligence" for discovering vertigo or a fall. The intelligence may, for example, be realized by means of a microcontroller or a programmable chip and thus analyses corresponding patterns of sounds or acceleration data which are able to predict as probable an imminent fall.

Additionally, the evaluating unit may comprise modules for triggering alarms in a wireless manner, for example an alarm signal transmitted to an external unit. This may, for example, take place by means of Bluetooth. The external unit may, for example, represent the alarm signal in an optical or acoustic manner, transmit a notification to a place of notification (like, for example, relatives or an emergency institution) and/or also record the alarm situation. Furthermore, in embodiments, the evaluating unit is able to store the data acquired and/or transfer same via a wireless connection to a corresponding storage medium so that losses in tone can be acquired for a certain period of time and thus provide evidence for the presence of a disease. The precise position of the combined sensor or the sensors on the body is, as has been mentioned, to be determined by suitable studies for specific cases of application and may be adapted as desired to the respective case of application. Positions of the sensors or the combined sensor as described here correspondingly only serve as examples and may correspondingly be optimized with regard to the effectivity of prediction.

Evaluating a measurement value may take place as follows. Both sensors provide their respective measurement values (sounds or sound patterns, acceleration values) to the microcontroller programmed correspondingly ("intelligence") which fuses the data on the basis of a physiological-physical model. The objective of fusing is discovering deviating body movements in the sense of a short loss of control of the spatial position and thus allowing recognition of vertigo or expected movement patterns. Thus, the microcontroller may, for example, record "normal" body movements which vary from human being to human being, over a certain period of time so that "abnormal" body movements which may be accompanied by a loss in tone may be determined using a comparison. Since the muscle tone also changes when, for example, sitting down, the very combination with the acceleration sensor is important in order to discover only certain events (like, for example, vertigo), but not natural patterns of behavior which have no pathological background nor can be attributed to tiredness.

As has been mentioned, acquiring the muscle tone may exemplarily be performed by evaluating the muscle sound associated thereto and the sound patterns thereof. These patterns or sound patterns reflect the respective degree of activity of the muscle. In order to achieve perfect focusing to the muscle or heart sounds, environmental sounds may be measured in parallel. Environmental sounds here include, for example, sounds that do not originate in the human body or in the muscle. After having taken into consideration the transfer characteristic (different microphone, attenuation of clothing, etc.), these may be subtracted from the signal of the body sounds acquired. This differential sound measurement achieved in this way increases the device's sensitivity considerably, but needs another microphone (at another position) for acquiring the environmental sounds. Alternatively, parasitic environmental sounds may also be filtered out using algorithmic methods.

Evaluating the data of the acceleration sensor will result in information on a course of the body position relative to the gravitational field. This means that the acceleration acting on the acceleration sensor represents superposition of the gravitational acceleration and the relative acceleration (relative to the gravitational field) of the human body or the acceleration sensor. In the case of a fall, the acceleration acting on the acceleration sensor will decrease at first (caused by the gravitational acceleration of the human body) and then, subsequently, be increased considerably at the time of hitting the ground. A noticeable swing in acceleration may thus be an indication of a fall occurring. Spontaneous alterations may correspondingly be recognized, as has just been described, and vertigo may be inferred form the patterns thereof.

With regard to fixing the sensors or the combined sensor to a patient, a practical realization is to be chosen such that both ergonomics requirements on the one hand and the need of acquiring measurement values reliably on the other hand are taken into account. Correspondingly, the place of fixing the sensors or the combined sensor may be selected in different ways, depending on the respective case of application. Apart from optimized fixing with respect to the desired application (discovering dizziness, discovering tiredness, discovering heart sounds or heart failure, etc.) already described, it should also be kept in mind when fixing the sensors that the patient is not limited in his or her freedom of movement in an unacceptable manner and that additionally the natural movement of the patient does not influence fixing of the sensors negatively (strong hold also with natural movements).

Compared to conventional methods, evaluating two modalities of only indirect dependencies increases the reliability of the system and offers, as has been mentioned, a way of predicting a potentially imminent fall or other events which are accompanied by a momentary loss in tone. Examples of this include acute fatigue symptoms, clarifying unclear symptoms of cardiological origin, detecting motor diseases or states of fatigue.

Embodiments of the present invention are thus of advantage compared to the conventional art because acquiring an acceleration is combined with acquiring sounds of the muscular system or of a certain muscle. Thus, the exclusive acquisition of an acceleration of the conventional art is combined with sound acquisition in an intelligent manner. Since an imminent muscle tone weakening already becomes evident from a sound pattern of the muscular system, it is, in particular, possible to achieve a warning beforehand, which conventional methods or processes cannot offer. Thus, an inventive device can be employed in a practical manner not only for predicting falls or vertigo, but also for giving timely warning in the case of signs of tiredness, which represents a special safety hazard in particular for drivers of a vehicle. When permanently recording measurement data, losses in tone, distributed over a day, of a certain muscular system can be examined and recorded, which may provide further insight into certain diseases.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
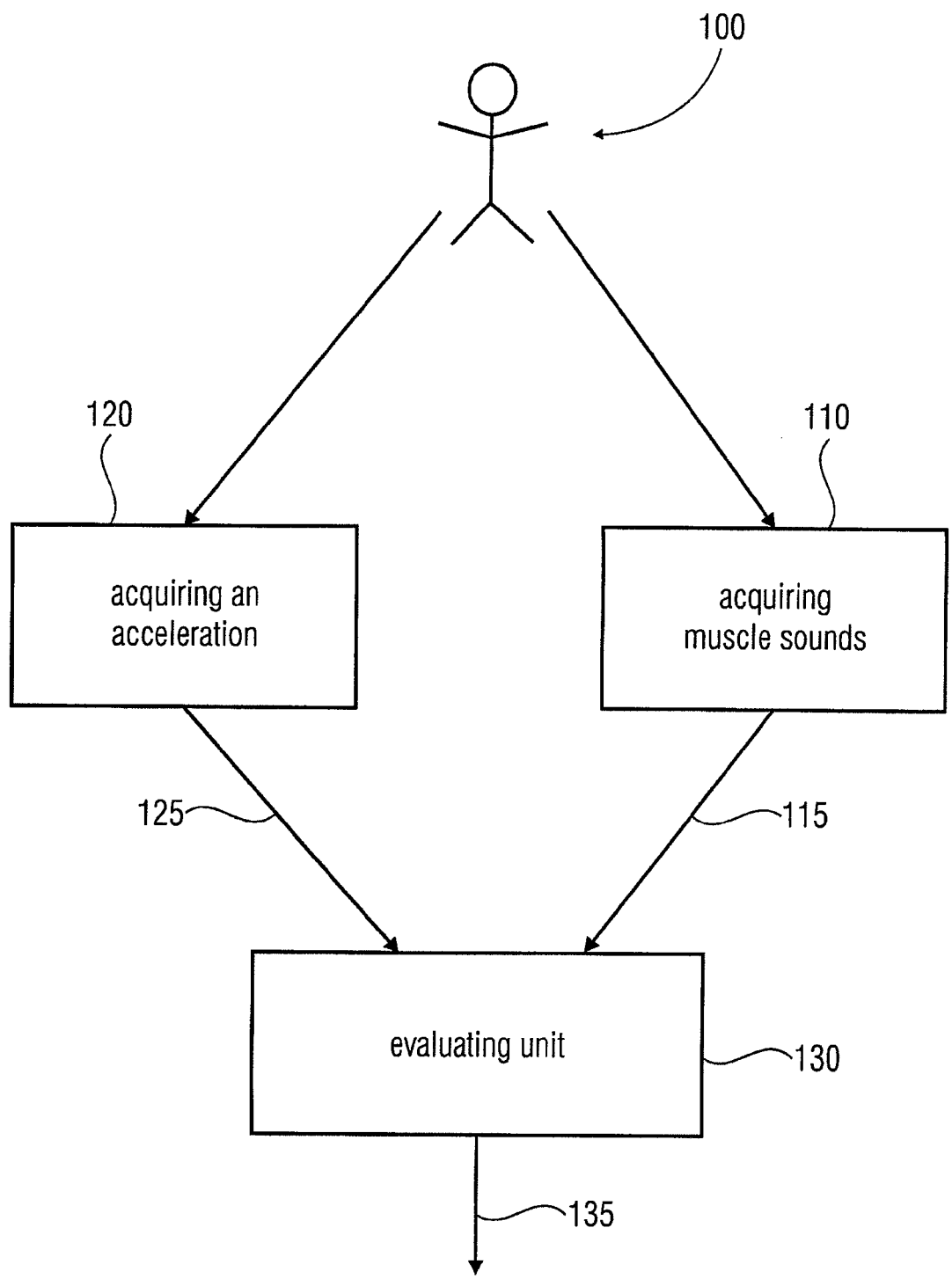
FIG. 1 shows a schematic illustration of acquiring measurement values in a human being and evaluating same.

With regard to the subsequent description, it should be kept in mind that same functional elements or functional elements having the same effect are attributed the same reference numerals in different embodiments and the descriptions of these functional elements in the different embodiments explained below are mutually interchangeable.

FIG. 1 shows acquiring measurement values in a human being 100 or another living body, which includes acquiring muscle sounds by a sound sensor 110 on the one hand and includes acquiring an acceleration by an acceleration sensor 120 on the other hand. The sound sensor 110 may, in the easiest case, exemplarily comprise a microphone transmitting signals 115 to an evaluating unit 130. The acceleration sensor 120 acquires a relative acceleration to the gravitational acceleration and the body's own acceleration resulting from variations in tone and transmits respective acceleration data 125 to the evaluating unit 130. By combining both types of data and the timelines (patterns) thereof, the evaluating unit 130 establishes event data (warning signals) 135, wherein the event data 135 may, for example, be a sign of staggering, dizziness, vertiginous attacks, signs of tiredness, abnormal cardiac activity, etc. In further embodiments, further acceleration sensors and/or further sound sensors are attached to the human being, wherein the further acceleration sensors are able to acquire accelerations of further body parts of the human being 100 and the further sound sensors are able to acquire environmental sounds and/or sounds of other organs (heart), for example.

Figure 2A:
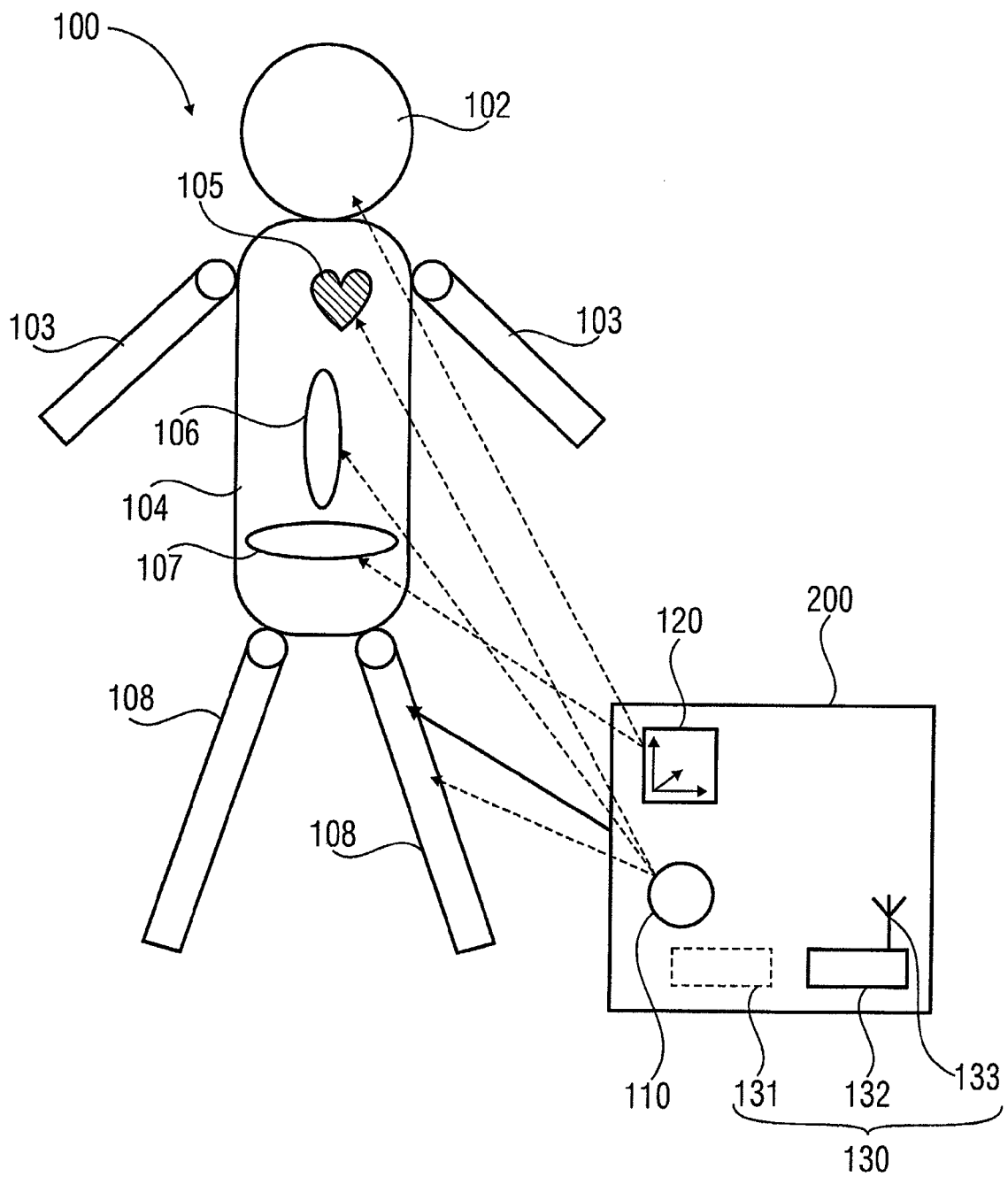
FIG. 2A shows a potential distribution of sensors at different positions of the human body.

FIG. 2A shows the human being 100 comprising a head-neck area 102, two arms 103, a torso 104 with a heart 105, a spine area 106; a hip area 107, and two legs 108. The sound sensor 110 and the acceleration sensor 120 may be attached to the human being 100 at different body regions or body positions (represented by broken lines). When the acceleration sensor 120 and the sound sensor 110 are accommodated in a combined sensor 200, the combined sensor may exemplarily be attached to a leg or thigh 108 (continuous line). The evaluating unit 130 may be arranged either in the sound sensor 110 or in the acceleration sensor 120 and may exemplarily comprise a microcontroller 131 (intelligence), a transfer unit 132 (exemplarily based on Bluetooth) and an antenna 133. The evaluating unit may also be arranged in the combined sensor 200 or its housing.

Figure 2B:
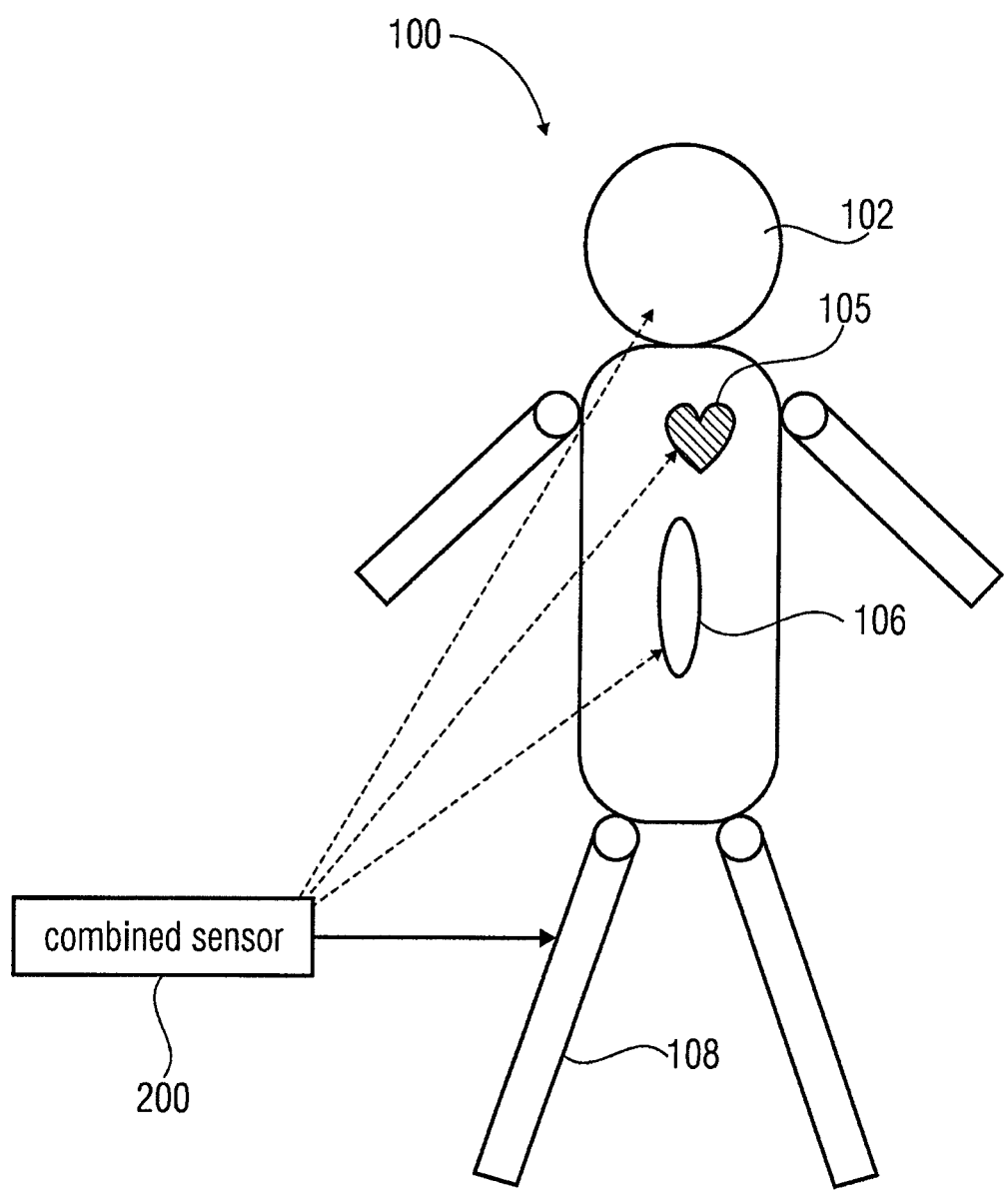
FIG. 2B shows potential positions of a combined sensor.

FIG. 2B shows potential positions of fixing the combined sensor 200, which may exemplarily be arranged on a leg 108 or the thigh. In addition, it is also possible to arrange the combined sensor 200 at another body position as long as this proves to be favorable for acquiring the data, for example, in a spine region 106 for acquiring sounds of the support muscles or close to the heart 105 for acquiring heart sounds or in the neck-head area 102, for example for acquiring signs of tiredness (head nodding). These alternative arrangements are characterized by broken lines.

Figure 2C:
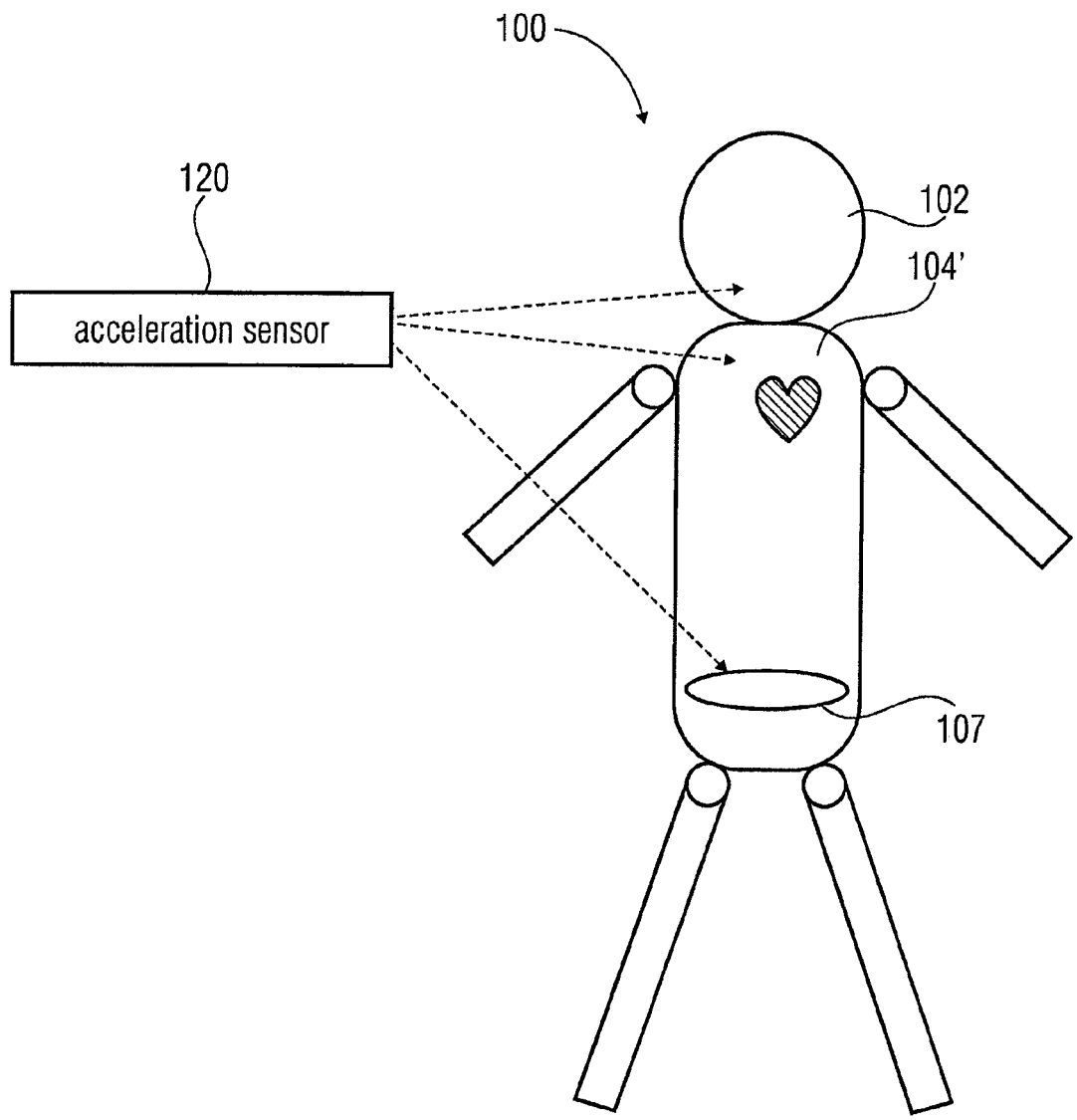
FIG. 2C shows potential positions of an acceleration sensor.

FIG. 2C shows potential positions for fixing the acceleration sensor 120. These positions refer in particular to a case in which the acceleration sensor 120 and the sound sensor 110 are arranged separately at different body positions. The acceleration sensor 120 may exemplarily be arranged in the hip area 107, the neck-head area 102 or a shoulder area 104'.

Figure 2D:
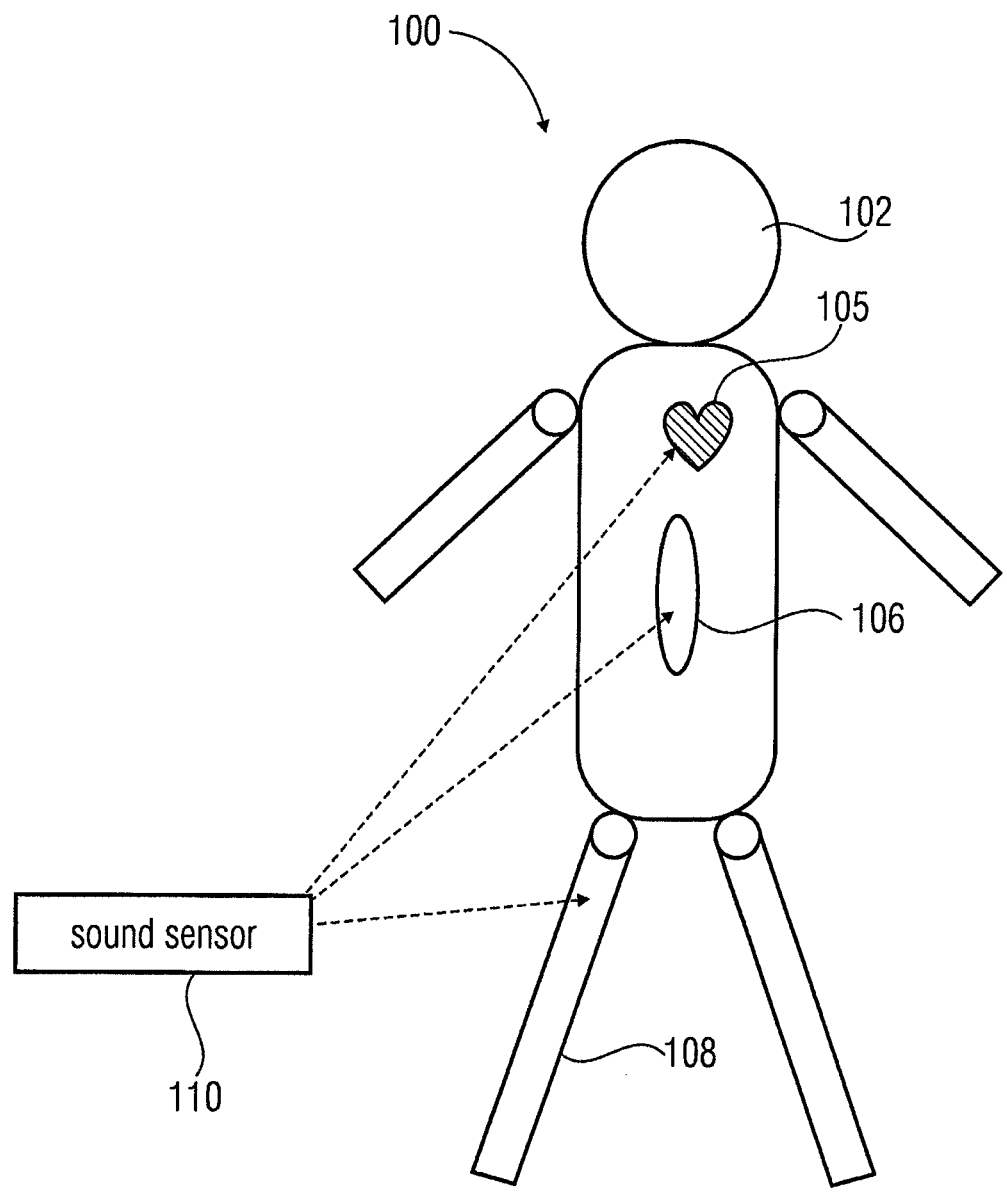
FIG. 2D shows potential positions of a sound sensor.

FIG. 2D shows potential arrangements of the sound sensor 110, wherein, like in FIG. 2C, in this embodiment, it is assumed that the sound sensor 110 and the acceleration sensor 120 are fixed to the human body 100 separately. Potential arrangements of the sound sensor 110 here are the thigh or the leg 108, the spine area 106, close to the heart 105 or other areas of the human body (exemplarily the head-neck area 102) not shown in FIG. 2D.

In the embodiments of FIGS. 2C and 2D, the evaluating unit 130 may be arranged either in the sound sensor 110 or the acceleration sensor 120 or in the housing thereof. Thus, the submodules, namely the microcontroller 131 ("intelligence") and the transfer unit 132 (Bluetooth), are integrated, in accordance with ergonomic aspects, into all of the sensors in the case of individual sensors or, in the case of a combined sensor, into the housing thereof. In order to be able to communicate with each other, the separately arranged sensors (sound sensor 110 and acceleration sensor 120) each need a transfer unit 132 so that data can be exchanged. Transfer may take place in a wired or wireless manner. On the other hand, it may be sufficient for the microcontroller 131 to be integrated only into one of the sensors (or the housing thereof). It is also possible, using the transfer units 132, to transfer the data to an external unit, wherein the external unit may also be fixed to the human being or to a different place (also further away from the human being). By using several acceleration sensors, if also possible to increase measuring precision, wherein acceleration sensor may exemplarily be arranged in the hip area 107 and the shoulder area 104'.

For attaching or fixing, the combined sensor 200 or the acceleration sensor 120 and/or the sound sensor 110 and/or the evaluating unit 130 may comprise means for fixing or means for attaching which in turn exemplarily comprise a Velcro fastening, glue, or rubber fastening.

Different embodiments of how data acquisition and evaluation may take place are described below. The easiest case where only sound data are acquired will be described at first in FIG. 3, whereas FIG. 4 describes parallel acquisition and evaluation, which is more complicated but offers a number of advantages.

Figure 3:
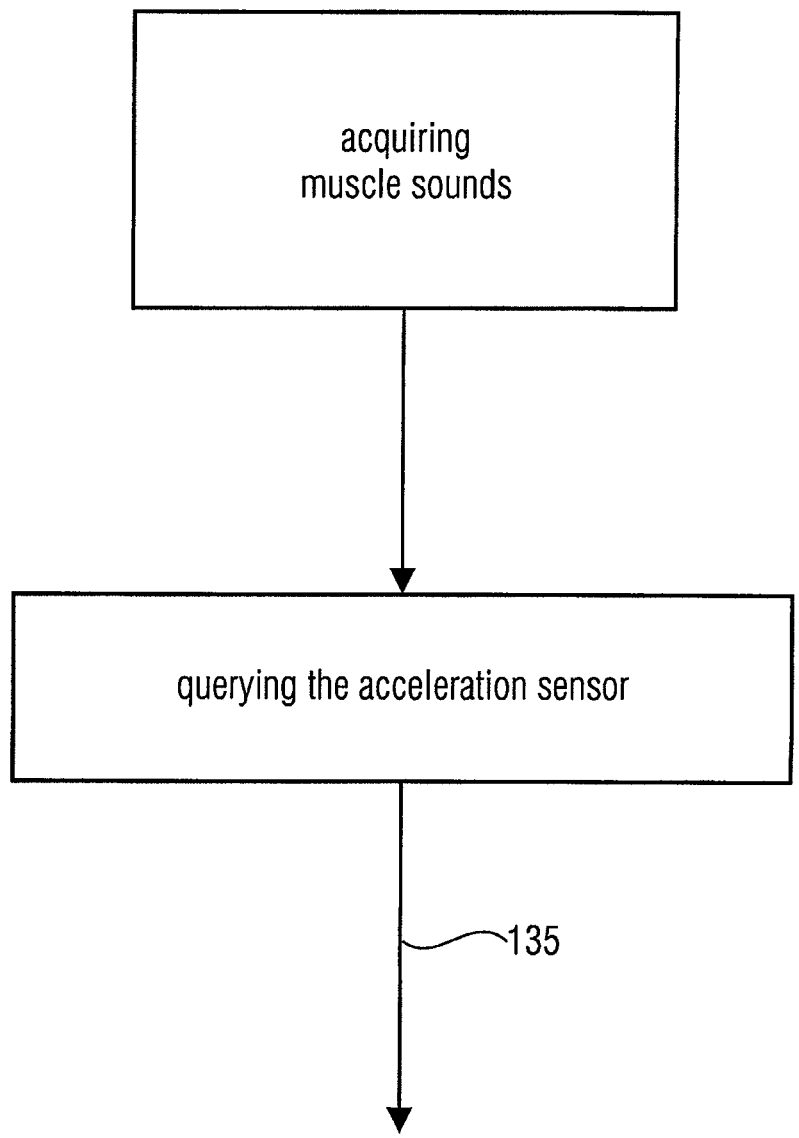
FIG. 3 shows potential combined data acquisition.

FIG. 3 shows an embodiment of a method in which the muscle sounds are acquired permanently (continually) or at regular time intervals, for example, and a query signal 115' is only generated when peculiarities which are accompanied by a loss in tone arise. In this case, querying the acceleration sensor 120 takes place and only when the acceleration sensor 120 also determines peculiarities, for example within a predetermined time interval (time window), like, for example, staggering, head nodding, will the warning signal 135 or the event data be output. The time window may exemplarily comprise 0.1 seconds, 0.5 seconds, 1 second or 5 seconds. As long as the acceleration sensor 120 does not discover any peculiarities within the time window, the sound signal, for example, may be ignored.

Figure 4A:
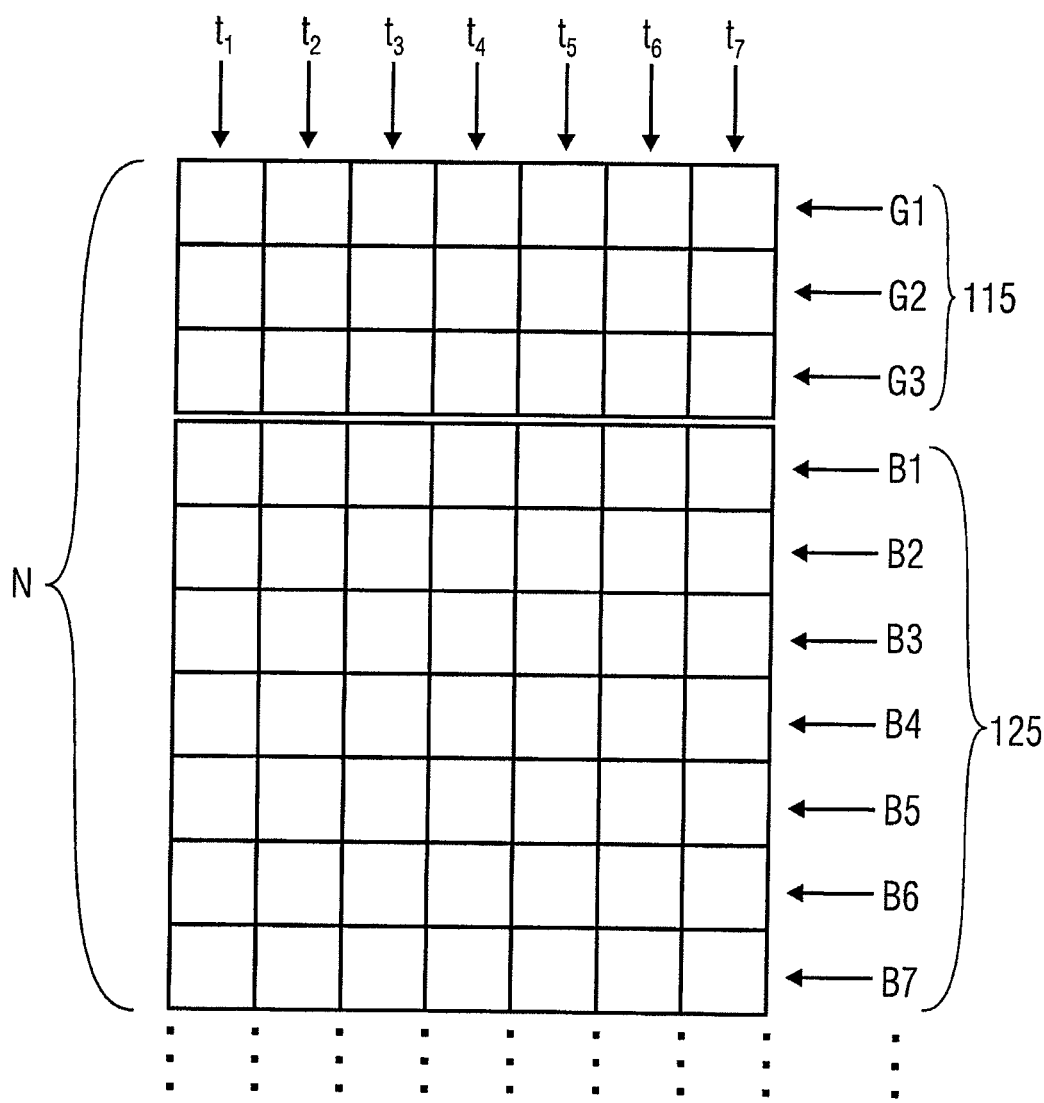
FIGS. 4A-C show embodiments of evaluating acceleration and sound data.
Figure 4B:
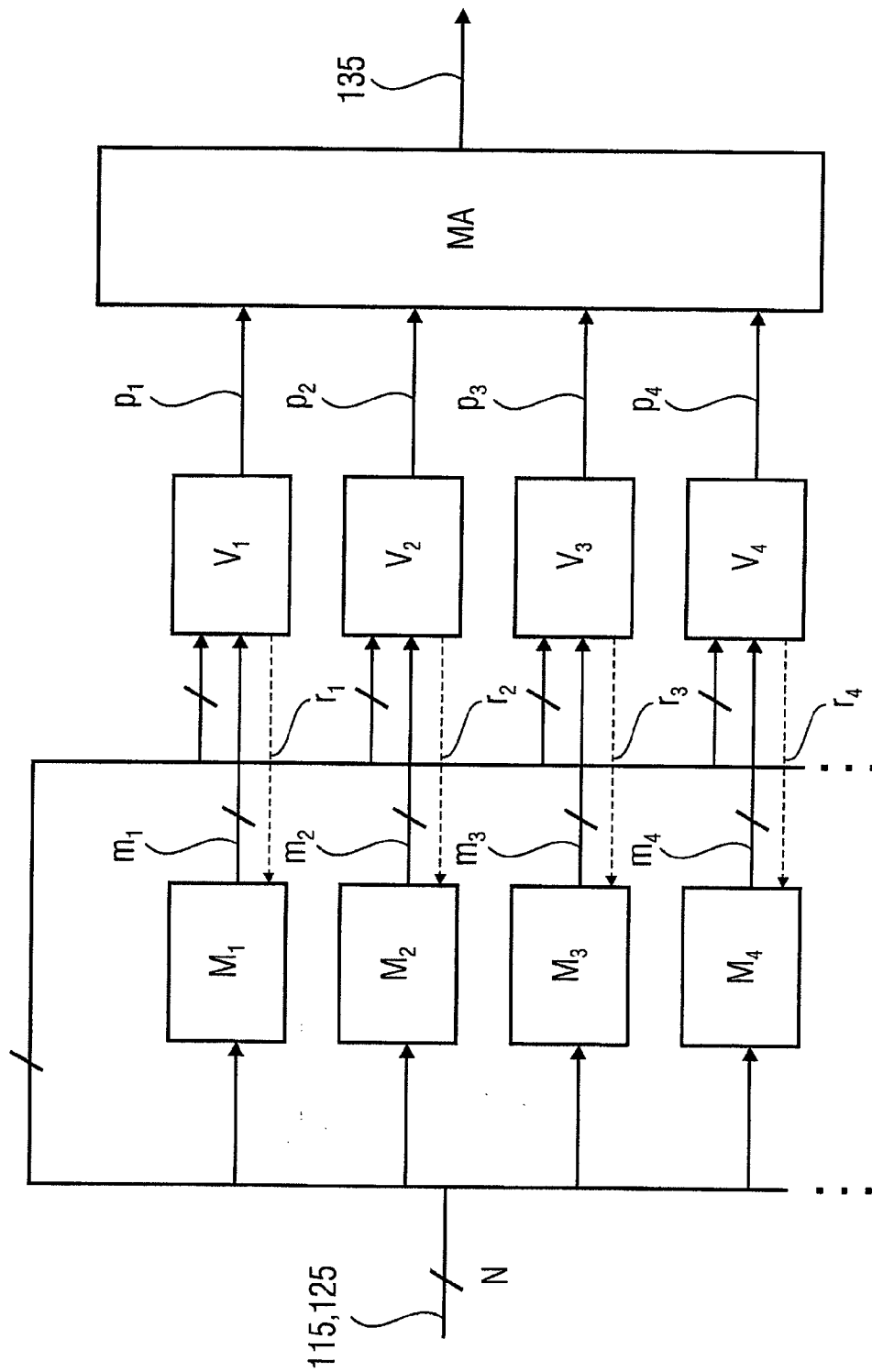
Figure 4C:
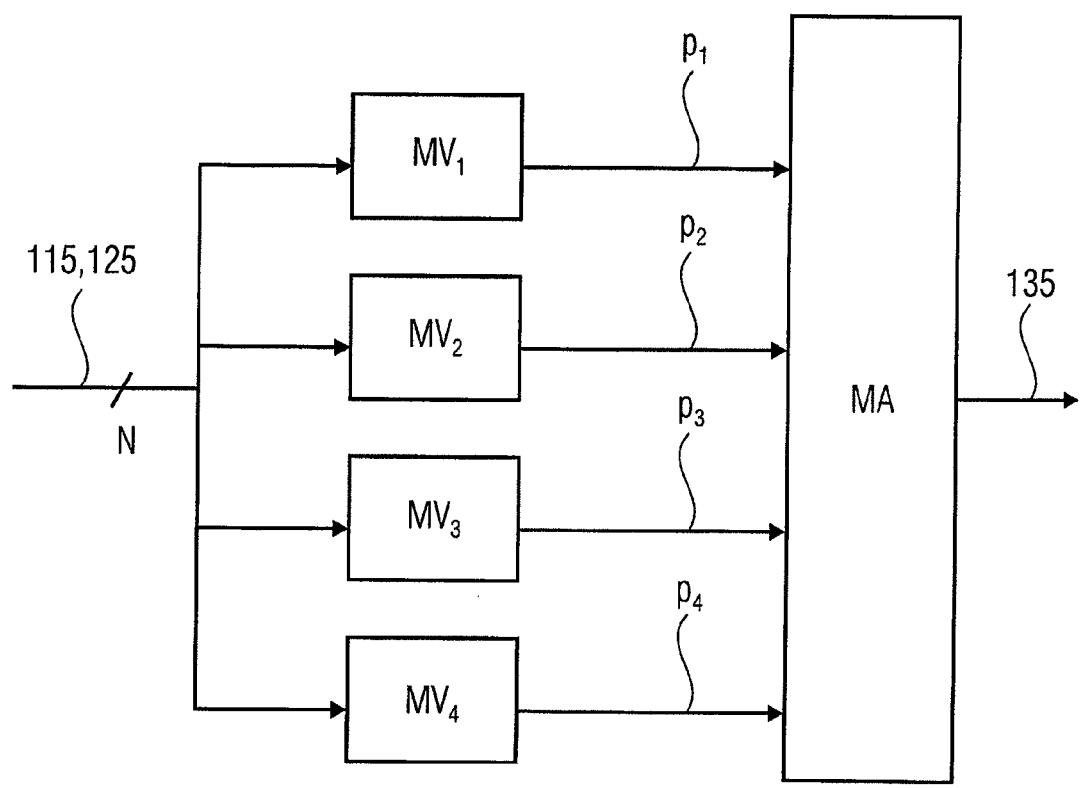

FIGS. 4A to 4C describe potential embodiments of the evaluating unit 130, FIG. 4A at first describing the data structure by means of which the evaluating unit 130 can analyze data and draw respective conclusions (generating a warning signal, notifying a notification institution, etc.).

The evaluating unit 130 at first receives the acceleration data 125 from the acceleration Sensor(s) 120 which may refer to several accelerations (like, for example, accelerations along different spatial directions) or accelerations relating to different acceleration sensors 125. In FIG. 4A, an example is shown in which seven pieces of acceleration data 125 are acquired, of which, for example, three acceleration values B1, B2, B3 refer to the three spatial directions of the acceleration of, for example, the hip, three further acceleration values B4, B5, B6 refer to the three spatial directions of the acceleration of the shoulder area 102, and three further accelerations B7, B8, B9 (B8 and B9 are not shown in FIG. 4A) refer to the three spatial directions of the acceleration of the thigh 108. The acceleration data indicated here only represent examples and generally only one or two or all three accelerations (relating to all three spatial directions) can be acquired for every acceleration sensor 125. Furthermore, further or fewer acceleration sensors 125 may be used. In addition, the data set as shown in FIG. 4A includes three pieces of sound data G1, G2, G3 which may exemplarily correspond to a sound of the thigh muscle 108, the cardiac muscle 105 and the environmental sound.

Generally, N pieces of data are acquired, wherein in further embodiments a greater or smaller number of pieces of data than shown may be acquired. This allows predicting or detecting critical states more precisely or, on the other hand (when acquiring fewer pieces of data), reducing the calculating complexity of the evaluating unit 130.

The sound and acceleration data 115, 125 may still be acquired at different points in time. One set of data may exemplarily be acquired at a first time $t_1$, a second time $t_2$, a third time $t_3$, ... up to a seventh time $t_7$, wherein the time rhythm or clock rhythm in which data are acquired may be adapted to the given situation. Exemplarily, data may be acquired with a clock of seconds or with a clock in a range between $\frac{1}{15}$ and 2 seconds. In further embodiments, this clock may be adjusted variably so that a critical state can be discovered efficiently in a manner adapted to the respective situation (faster or slower movement).

FIG. 4B shows how the sound data 115 and the acceleration data 125 can be processed in the evaluating unit 130, wherein the number of data acquired at a certain point in time is referred to by N. In the embodiment of FIG. 4B, the speed and acceleration data 115, 125 are at first input into a first model unit $M_1$, into a second model unit $M_2$, into a third model unit $M_3$, and into a fourth model unit $M_4$ and the model units $M_i$ (i=1, 2, 3, 4, ...) exemplarily acquire the data in the manner as is illustrated in FIG. 4A, which means that, for example, data are acquired in a predetermined clock at predetermined times $t_n$, so that the matrix shown in FIG. 4A results where the different data are written to different lines and data acquired at different points in time are arranged in different columns.

The different model units $M_i$ are based on different models, wherein the models may refer to different activities of the human being which may exemplarily include walking, climbing stairs, running or cycling, or other activities. In addition, a model may relate to a case of emergency, i.e. simulate a typical fall pattern. Taking the data at the exemplary times $t_1$ to $t_n$ as a basis, a data set for the following time $t_{n+1}$ can be calculated using the models. This may exemplarily be performed by means of a convolution. The data set calculated in advance thus corresponds to the most probably state the system will take in the following time $t_{n+1}$ using the corresponding model. The data $m_i$ (i=1, 2, 3, 4, ...) calculated in advance or estimated in this way are input into comparative units $V_i$, the comparative unit $V_i$ comparing the data $m_i$ calculated in advance relating to the time $t_{n+1}$ to the actually measured data at the time $t_{n+1}$. The comparative units $V_i$ provide, as an output, percentage values $p_i$ by which the model taken as a basis matches the actually measured values. The percentage values $p_i$ achieved in this way are subsequently read into a model selection unit MA and the model selection unit MA, using the percentage numbers $p_i$ received, chooses that model of the highest percentage matching with the actually measured values.

A given model, like, for example, a human being 100 walking, may exemplarily take place at different speeds. Consequently, it is practical for the comparative units $V_i$ to comprise feedback in order to be able to change the model used or a parameter of the model used correspondingly. This feedback may take place using feedback data $r_i$ and may contain a parameter (for example temporal extension or temporal compression) by which the basic model is changed. This parameter $r_i$ may exemplarily be determined by the comparative unit $V_i$ optimizing the parameters on which the model is based, so that the percentage matching $p_i$ will be maximized. For the example given of a human being 100 walking, this may take place such that the walking speed of the human being 100 will be varied by the comparative unit $V_i$ until the percentage matching $p_i$ has a maximum value.

FIG. 4C shows another embodiment of evaluating sound and acceleration data 115, 125. Again, it is assumed that the data set contains a total number of N pieces of data which are acquired one after the other at certain points in time $t_n$ (n=1, 2, 3, ...). In the embodiment, as is shown in FIG. 4C, these data sets are input into model test units $MV_i$, wherein it is assumed in this embodiment that there are four model test units $MV_i$, the number of which, however, may vary in other embodiments. The model test units $MV_i$ will then again acquire the sound and acceleration data 115, 125 in a manner as is shown in FIG. 4A, so that the result will be a matrix comprising N lines and n columns, wherein data of different kinds are arranged in different lines and data at different points in time are arranged in different columns of the matrix. The matrix of data achieved in this way then has a characteristic pattern for every, activity or movement of the human being 100 (wherein the characteristic pattern again may be temporally compressed or extended).

The model test units $MV_i$ will then test the data pattern acquired by the different models, i.e. the model test unit $MV_1$ compares the data acquired (i.e. the data in the matrix as is illustrated in FIG. 4A) to the first model, the second model test unit $MV_2$ tests the data set using the second model, etc. Generally, the model test units $MV_i$ will not achieve 100% matching of the data sets measured or the data matrix of FIG. 4A and the data structures on which the models are based and the model test units $MV_i$ will output a percentage matching value $p_i$. The percentage matching value $p_i$ indicates to which percentage the actually measured data or the data matrix matches the basic model or models. The model test units $MV_i$ may thus again vary parameters of the basic model internally, with the goal of maximizing the percentage matching values $p_i$ achieved. The percentage matching values $p_i$ achieved in turn are input into a model selection unit MA, the model selection unit MA in turn selecting that model of the best possible matching of the data matrix measured and the basic model.

Parallel acquisition of the data or parallel adjusting of the data acquired to the basic models allows that a change in the activity of the human being 100, for example from walking to climbing stairs or to sitting down, is evident from the percentage matching values $p_1$ changing abruptly so that the model selection unit MA may adapt the basic model dynamically. However, when the model selection unit MA recognizes a data pattern indicating a critical state (for example the fall or vertigo model), the model selection unit MA may output a warning signal 135 or transfer a corresponding notification to an emergency institution (notification institution). When referring to the driver of a vehicle, the model selection unit MA may, when determining a state (or model) indicating over-tiredness of the driver of the vehicle (for example head nodding), output a corresponding warning signal to the driver of the vehicle to make him or her aware of the critical state.

A Kalman filter may exemplarily be applied when evaluating the data sets or the data matrix in the evaluating unit 130. Based on the models given; a Kalman filter utilizes an equation of state using which future states of the system can be estimated. This is particularly practical since a Kalman filter offers a way of filtering out corresponding errors or noise and is further predestined for real-time applications. In addition, it is possible using a Kalman filter to change the model dynamically using parameter changes in order to achieve better matching of the estimated states and the actual states.

It may be practical in further embodiments for not all the models to be processed in parallel using the same intensity, but, in periods in which a given model describes the situation very well, for other models to be tested in greater time intervals and, only with a potential change in model, due to greatly decreasing matching probabilities $p_i$, the alternative models to be tested again at full intensity. It is also possible to test only one model at a certain time with regard to matching with the actually measured values and to only test other models one after the other when the matching probabilities $p_i$ are below a certain threshold. This may take place until one model turns out to be dominating again. In further embodiments, the evaluating unit 130 adapts the model to the natural characteristics of the human being 100. Thus, using such intelligence, each of the models (like, for example, walking, climbing stairs, standing, lying, etc.) will adapt to the individual human being 100 after some time.

Thus, embodiments of the present invention particularly refer to a method and a device for discovering a loss in tone or an imminent loss in tone of a muscle system of a human being. Embodiments comprise different combinations of measurement value recorders (sound sensors 110 and acceleration sensors 120) which may be arranged at different body positions individually or several ones together and, additionally, embodiments offer a method for discovering a state of vertigo or signs of tiredness and other states of the human body resulting in an imminent loss in tone, wherein a corresponding algorithmic method may be used. The corresponding algorithmic method exemplarily assumes coincidence of two events, occurrence of corresponding muscle sounds on the one hand and acquiring a corresponding acceleration (an acceleration threshold value or pattern) on the other hand, exemplarily as a consequence of a fall, head nodding or other sudden body movements. The corresponding muscle sounds may exemplarily correspond to a sound threshold value or leaving a bandwidth (like, for example, in frequency representation) of the sound pattern. Thus, the device is sensitive with regard to strongly increased or strongly decreased muscle sounds. The acceleration threshold value may, for example, correspond to the human body 100 impacting or other abrupt body movements (head nodding).

In contrast to conventional methods or devices which are based only on acquiring acceleration data, embodiments of the present invention thus offer a greater degree of security and reliability with regard to the detection of pathological or undesired states of the human body.

It is in particular pointed out that, depending on the circumstances, the inventive scheme may also be implemented in software. The implementation may be on a digital storage medium or on a non-volatile flash memory, in particular on a disc or a CD comprising control signals which may be read out electronically which can cooperate with a programmable computer system such that the corresponding method will be executed. Generally, the invention thus also is in a computer program product comprising program code stored on a machine-readable carrier for performing the inventive method when the computer program product runs on a computer. Expressed differently, the invention may also be realized as a computer program having a program code for performing the method when the computer program runs on a computer or a so-called embedded system.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. A device for predicting a loss of control over a muscle of a human being, comprising:
   a detector for detecting a muscle sound;
   an acquirer for acquiring an acceleration of the human being; and
   an evaluator for evaluating the muscle sound and the acceleration and determine an imminent loss of control over the muscle from the muscle sound and the acceleration.

2. The device in accordance with claim 1, wherein the detector for detecting is implemented to detect the muscle sound of a supportive muscle or a leg muscle, and wherein the evaluator for evaluating is implemented to determine an imminent loss of control of the supportive muscle or the leg muscle.

3. The device in accordance with claim 1, wherein the evaluator for evaluating is implemented to output, in the case of determining an imminent loss of control over the muscle, a warning signal detectable by the human being.

4. The device in accordance with claim 3, wherein the warning signal comprises a photo signal and/or an acoustic signal and/or a tangible stimulus.

5. The device in accordance with claim 3, wherein the evaluator for evaluating is implemented to transfer the warning signal to a predetermined notification institution.

6. The device in accordance with claim 1, wherein the evaluator for evaluating is implemented to acquire the muscle sound and the acceleration at a sequence of time instances and combine same to form a data set.

7. The device in accordance with claim 6, wherein the evaluator for evaluating is implemented to compare the data set to a model data set and to determine a percentage matching value to draw conclusions about a current movement of the human being, the model data set corresponding to a data set which may be generated by a certain movement of the human being.

8. The device in accordance with claim 7, wherein the model data set comprises a parameter, and wherein the evaluator for evaluating is implemented to vary the parameter in order to maximize a percentage matching value.

9. The device in accordance with claim 1, wherein the evaluator for evaluating is implemented to store data of the detector and/or data of the acquirer.

10. The device in accordance with claim 1, wherein the evaluator for evaluating comprises a transferrer and the transferrer is implemented to acquire data from the detector and/or data from the acquirer and transfer same to a central unit.

11. The device in accordance with claim 10, wherein the transferrer acquires data in a wireless manner or transfers data in a wireless manner.

12. The device in accordance with claim 1, wherein the detector for detecting and the acquirer for acquiring and the evaluator for evaluating are housed together in a combined sensor.

13. The device in accordance with claim 12, wherein the combined sensor comprises an attacher for attaching to a thigh or leg of the human being.

14. The device in accordance with claim 1, wherein the detector for detecting comprises an attacher for attaching to a thigh and the acquirer for acquiring an acceleration comprises an attacher for attaching to a hip area of the human being.

15. The device in accordance with claim 1, further comprising a further acquirer for acquiring cardiac muscle sounds, wherein the further acquirer may be attached close to the heart of the human being and the evaluator for evaluating is implemented to perform determining the loss of control also from the cardiac muscle sounds.

16. The device in accordance with claim 1, wherein the detector for detecting and the acquirer for acquiring or the combined sensor comprise an attacher for attaching to a head-neck area to determine head nodding resulting from over-tiredness of the human being.

17. The device in accordance with claim 1, wherein the detector for detecting and/or the acquirer for acquiring comprise a wireless transmitter, the wireless transmitter being implemented to transmit sensor data to the evaluator for evaluating.

18. The device in accordance with claim 1, wherein the evaluator allows transmitting data by means of Bluetooth.

19. The device in accordance with claim 1, further comprising a further detector for detecting environmental sounds originating outside the human being, and wherein the evaluator for evaluating is implemented to receive data from the further detector and to form a sound difference between the muscle sounds and the environmental sounds.

20. The device in accordance with claim 1, wherein the acquirer for acquiring an acceleration is implemented to determine a timeline of the position of a torso of the human being relative to the gravitational field.

21. The device in accordance with claim 1, wherein the evaluator for evaluating is implemented to receive data of the detector at a sequence of time instances, and is further implemented to additionally receive, when reaching a sound threshold value, data from the acquirer for acquiring an acceleration in order to generate a warning signal when an acceleration threshold value is exceeded.

22. The device in accordance with claim 1, wherein the evaluator is implemented to continuously survey the muscle sound to identify an occurrence of irregularities in the muscle sound indicating the immanent loss of control over the muscle, and interrogate the acquirer responsive to the identification of the occurrence of irregularities in the muscle sound and check as to whether the acceleration of the human being shows particularities relating to the immanent loss of control over the muscle within a predetermined time interval after the occurrence of irregularities in the muscle sound, and disregard the occurrence of irregularities in the muscle sound in case of the acceleration of the human being showing no particularities relating to the immanent loss of control over the muscle within the predetermined time interval, and output, in the case of the acceleration of the human being showing the particularities relating to the immanent loss of control over the muscle within the predetermined time interval, a warning signal detectable by the human being.

23. The device in accordance with claim 1, wherein the evaluator is implemented to sample the muscle sound and the acceleration at a sequence of time instances and combine, for each time instance, the muscle sound and the acceleration sampled at the respective time instance to form a data set so as to obtain a sequence of data sets, the evaluator comprising a plurality of model units associated with different types of activities of the human being, each model unit being configured to subject the sequence of data sets to a prediction using a prediction model associated with the type of activity associated with the respective model unit;

a plurality of comparators, each comparator being associated with a different one of the plurality of model units and configured to compare the prediction of the associated model unit with the sequence of data units so as to obtain a percentage value for the associated model unit; and a model selector configured to select among the model units one for which the percentage value is maximum, wherein the different types of activities comprise at least one type of activity related to the imminent loss of control over the muscle.

24. The device in accordance with claim 23, wherein each of at least a subset of the plurality of model units are configured such that the prediction model associated with the type of activity associated with the respective model unit is parametrizable via a model parameter and the model parameter is adjusted using the percentage value for the respective model unit as a feedback.

25. The device in accordance with claim 1, wherein the evaluator is implemented to sample the muscle sound and the acceleration at a sequence of time instances and combine, for each time instance, the muscle sound and the acceleration sampled at the respective time instance to form a data set so as to obtain a sequence of data sets, the evaluator comprising a plurality of mode test units associated with different types of activities of the human being, each model test unit being configured to match temporal sub-sequences of the data sets out of the sequence of data sets with a pattern associated with the type of activity associated with the respective model unit to obtain a matching value for the respective model unit;

a model selector configured to select among the model test units one for which the matching value is maximum, wherein the different types of activities comprise at least one type of activity related to the imminent loss of control over the muscle.

26. The device in accordance with claim 25, wherein each of at least a subset of the plurality of model units are configured such that the pattern associated with the type of activity associated with the respective model test unit is parametrizable via a model parameter and configured to continuously adjust the model parameter so as to maximize the matching value obtained by the respective model test unit.

* * * * *